US00PP10077P

United States Patent [19]

Zerr

[11] Patent Number: Plant 10,077

[45] Date of Patent: Oct. 21, 1997

[54] POINSETTIA PLANT NAMED FISCOROSA

[75] Inventor: Katharina Zerr, Simmern, Germany

[73] Assignee: Florfis AG, Binningen, Switzerland

[21] Appl. No.: 600,233

[22] Filed: Feb. 12, 1996

[30] Foreign Application Priority Data

Feb. 15, 1995 [DE] Germany ..... EUP178

[51] Int. Cl.[6] ..... A01H 5/00

[52] U.S. Cl. ..... Plt./86.3

[58] Field of Search ..... Plt./86.3, 86.4

*Primary Examiner*—James R. Feyrer

*Attorney, Agent, or Firm*—Foley & Lardner

[57] ABSTRACT

A new and distinct cultivar of Poinsettia plant named Fiscorosa, characterized by its light pink bract color, brown elliptical bracts with weak lobes, uniform dark green, moderately lobed foliage, compact plant habit, and medium early flower response.

1 Drawing Sheet

The present invention relates to a new and distinct cultivar of poinsettia plant known by the cultivar name Fiscorosa, and botanically known as *Euphorbia pulcherrima*.

Fiscorosa is a product of a mutation program carried out by the inventor, Katharina Zerr, in Hillscheid, Germany, in 1994.

The primary objective of the induction program was to expand the bract color ranges of Fiscor, disclosed in U.S. Plant Pat. No. 9,364, and characterized by its red bract color, dark green foliage and comparatively compact habit.

The irradiation program comprised exposing rooted cuttings taken from plants of the parent cutivar to an X-ray source of 30 Gy dosage in Ahrensburg, Germany, under the supervision of the inventor.

The irradiated plants were grown out in a greenhouse in Hillscheid, Germany, and were subsequently asexually propagated by the inventor by taking cuttings. The plants resulting from these cuttings were screened for mutations as small flowering single stem plants in autumn 1994. Parts of plants showing a positive mutation were left to develop vegetative shoots which were used as cuttings and grown out.

Fiscorosa was derived from a plant with a ring of bracts partly turned pink. Its branches or side shoots were selected by means of their petiole color (which gives a hint of the bract color to be expected) and then used for asexual propagation, carried out by the inventor in Hillscheid, Germany. In this way, a uniform clone with pink bracts was developed as promptly as possible.

Horticultural trial cultivation, conducted in summer 1995 and, on a larger scale, in autumn 1995, confirmed that the combination of characteristics disclosed for Fiscorosa are firmly fixed and are retained through successive generations of asexual reproduction.

The following traits have been repeatedly observed and are determined to be basic characteristics of Fiscorosa which in combination distinguish this poinsettia as a new and distinctive cultivar:

1. Light pink bract color
2. Broad elliptical bracts with weak lobes.
3. Uniform dark green foliage, moderately lobed
4. Compact plant habit, with pinched plants having a comparatively broad plant habit
5. Medium early flower response Fiscorosa has not been observed under all possible environmental conditions. The phenotpe may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

The plants described were planted as rooted cuttings in 12 cm pots on August 24, pinched 14 days later, and grown at 20° C. minimum day and night temperature. The plants initiated flowers in natural short day conditions in autumn. Observations and measurements were mainly taken at the beginning of flowering.

Of the many commercial cultivars known to the inventor, the most similar in comparison to Fiscorosa are the parent cultivar Fiscor and the commercial cultivars Lilo Pink and Freedom Pink.

In contrast to the red colored parent cultivar Fiscor, Fiscorosa has light pink colored bracts and light brownish pink colored petioles. The plant habit and shape of leaves and bracts of Fiscorosa are very close to Fiscor.

In comparison to Lilo Pink, Fiscorosa has a ligher shade of pink bract color, a broader plant habit, a flower response which is not as early as Lilo Pink, and better cyathia retention.

In comparison to Freedom Pink, Fiscorosa has smaller bracts with a more smooth surface, a later flower response, and its cyathia hold longer.

The accompanying color photographic drawing shows typical inflorescence and foliage of Fiscorosa, with colors being as true as possible with illustrations of this type. The photograph shows a typical mature potted plant.

In the following description, color references are made to The Royal Horticultural Society Colour Chart. The color values were determined indoors in a north light.

Classification:

*Botanical.*—*Euphorbia pulcherrima.*

*Commercial.*—Poinsettia, cv. Fiscorosa.

Parentage: Induced mutation of Fiscor.

Plant description:

*Form.*—Compact, medium height; pinched plant are bushy and broad.

*Growth habit.*—Medium growth. Height (above the soil line): 22 cm. Width: 50 cm. Branches: 5.5 on average.

Rooting: Medium, 20–24 days.

Blooming habit: Under natural short day conditions around December 1; 9–10 weeks of response time; saleable about 1 week before cyathia open.

Foliage:

*Size.*—Leaf blade: Length: 12.5 cm. Width: 7.5 cm.

*Color.*—Generally dark green. Upper surface: about 139 A. Lower surface: about 137 B.

*Leaf petiole.*—Brownish pink, about 179 C, petiole 7 cm in length.

*Shape.*—Broad elliptical, with weak lobes and rounded base.

*Texture.*—Surface smooth and flat.

*Edge of margin.*—Entire.

Flowering description:

*Cyathia.*—10–14 in number, in a narrow cluster; retention is medium.

*Bracts.*—Shape: Larger bracts are ovate or broad elliptical, with weak lobes and rounded base, flat. Size: Largest bract, including petiole: 15.5 cm.

Color: Generally light pink. Medium sized mature bract: 52 B. Lowest bract: 51 C. Aspect: Horizontal.

Reproductive organs:

*Nectar cups.*—Small to medium size, yellow-orange.

*Stamens.*—Pink filaments.

*Pollen.*—Yellow.

*Styles.*—Pink stripes, 6-lobed stigma.

*Ovaries.*—Light to medium green, top pink triangular, 3-celled, 3 ovules.

I claim:

1. A new and distinct cultivar of Poinsettia plant named Fiscorosa, as illustrated and described.

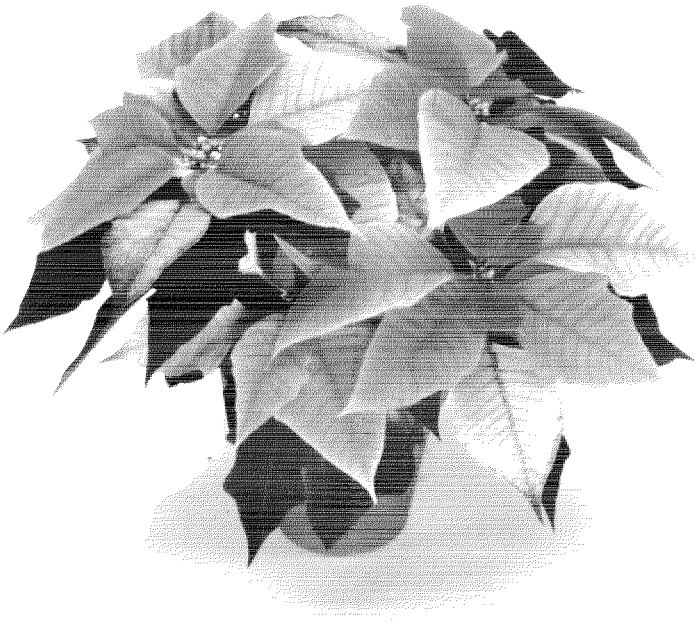

* * * * *